United States Patent [19]

Hamada et al.

[11] 4,335,049
[45] Jun. 15, 1982

[54] PROCESS FOR PRODUCING 5-METHYLFURFURAL

[75] Inventors: Kazuhiko Hamada; Goufu Suzukamo, both of Ibaraki; Koichi Fujisawa, Toyonaka, all of Japan

[73] Assignee: Sumitomo Chemical Company, Limited, Osaka, Japan

[21] Appl. No.: 279,004

[22] Filed: Jun. 30, 1981

[30] Foreign Application Priority Data

Jul. 16, 1980 [JP] Japan .............................. 55-98086
Mar. 19, 1981 [JP] Japan .............................. 56-41111
Mar. 20, 1981 [JP] Japan .............................. 56-41024

[51] Int. Cl.$^3$ ........................................ C07D 307/46
[52] U.S. Cl. ................................................ 549/483
[58] Field of Search ................................ 260/347.8

[56] References Cited
U.S. PATENT DOCUMENTS 4,154,744  5/1979  Hamada et al. ................ 260/347.8

FOREIGN PATENT DOCUMENTS 53-46961  4/1978  Japan .
53-50155  5/1978  Japan .

OTHER PUBLICATIONS

Org. Syn. Coll., vol. 2, 393–395 (1943).
J. Org. Chem., vol. 22, 1269–1270 (1957).
"Collected Lecture Manuscripts, Part II" of Joint Mass Meeting at the 42nd Autumn Meeting of the Chemical Society of Japan.

*Primary Examiner*—Richard Raymond
*Attorney, Agent, or Firm*—Stevens, Davis, Miller & Mosher

[57] ABSTRACT

A process for producing 5-methylfurfural by reducing 5-chloromethylfurfural which is used as a starting material or to be obtained by decomposing glucides commercially available more cheaply with hydrochloric acid, with hydrogen in an organic solvent in the presence of a palladium catalyst.

6 Claims, No Drawings

PROCESS FOR PRODUCING 5-METHYLFURFURAL

The present invention relates to a novel process for producing 5-methylfurfural useful as an intermediate for the production of medicines, agricultural chemicals, perfumes and the like.

More particularly, it relates to a process for producing 5-methylfurfural by reducing 5-chloromethylfurfural which is used as a starting material or to be obtained by decomposing glucides commercially available more cheaply with hydrochloric acid, with hydrogen in an organic solvent in the presence of a palladium catalyst.

For producing 5-methylfurfural, for example, the following processes are hitherto well known:

(1) A process in which fructose is heat-treated in the presence of hydrochloric acid and then reduced with stannous chloride [Org. Syn. Coll., Vol. 2, 393 (1943)]. This process is accompanied by gelation and solidification of humus during reaction, and requires more than an equivalent amount of stannous chloride, and therefore it is not practical as a commercial process and also its yield is as low as 20 to 22%.

(2) A process in which deoxysugar, repesented by L-rhamnose, or its glycosides are decomposed with an acid. Since deoxysugar is less easily obtainable in large quantities and in low costs and the yield is generally low, this process is not always suitable as a commercial one.

(3) A process in which 5-methylfuran, N,N-dimethylformamide and phosphorus oxychloride or phosgene are brought into reaction [J. Org. Chem., 22, 1269 (1957) and etc.].

5-Methylfuran is less easily obtainable also in this process, and more than equivalent amounts of expensive and strongly poisonous phosphorus oxychloride, phosgene and N,N-dimethylformamide should be used, and therefore this process is not always said to be suitable as a commercial one.

Previously, the inventors found a process for producing furan derivatives in a high yield and with high selectivity from glucides such as monosaccharide, disaccharide and etc., and applied for a patent (U.S. Pat. No. 4,154,744).

The inventors made a further study on an advantageous process to produce 5-methylfurfural, and found the followings: When 5-chloromethylfurfural is used as a starting material and reduced with hydrogen using a palladium catalyst in a certain organic solvent or inert organic solvent containing a basic additive, or when monosaccharide, disaccharide or isomerized saccharide is decomposed with hydrochloric acid in a system comprising water, an inert organic solvent and a catalytic amount of a surface active agent, and then after a basic additive is added to the hydrochloric acid-acidic organic layer which has been separated from the aqueous layer, is reduced with hydrogen in the organic layer using a palladium catalyst, 5-methylfurfural can be obtained from the above any starting material in one step, in a high yield and with high selectivity without damaging the aldehyde group and furan structure of the starting material. The inventors thus attained to the present invention.

That is, it was found that, when 5-chloromethylfurfural, obtainable as a well-known compound or by decomposition of glucides, commercially available more cheaply, with hydrochloric acid, is reduced with hydrogen using a palladium catalyst in a certain organic solvent or inert organic solvent containing a basic additive, the selective hydrogenolysis of the 5-chloromethyl group proceeds without being accompanied by saturation of the carbon-carbon double bond of the furan ring, cleavage of the furan ring and reduction of the aldehyde group, and as a result, that the objective 5-methylfurfural can be obtained in a high yield and with high selectivity.

Originally, benzyl halides, vinyl halides and allyl halides will be more easily hydrogenolyzed than alkyl halides, and also when allyl halides are reacted with hydrogen over a palladium catalyst, saturation of the carbon-carbon double bond proceeds, and so long as the reaction is not disturbed, the saturation is generally accompanied by hydrogenolysis of allyl halides. Considering this well-known technical knowledge, it is a novel discovery that, when compounds having such a structure as 5-chloromethylfurfural (furan ring, aldehyde group) are reduced with hydrogen in an organic solvent using a palladium catalyst, they should be able to be selectively hydrogenolyzed at the 5-chloromethyl group alone without being accompanied by any side reaction.

It is of great significance that the commercial production of an important intermediate for medicines, agricultural chemicals, perfumes and the like, which has so far been demanded, was made possible using abundant and cheap glucides as starting materials, on the basis of the novel discovery on the decomposition of glucides with hydrochloric acid/hydrogenolysis by means of the novel reaction system of the present invention.

In practising the process of the present invention, when already well-known 5-chloromethylfurfural is used as a starting material, it is reduced into 5-methylfurfural with hydrogen in an organic solvent using a palladium catalyst. As the organic solvent, those which are capable of dissolving 5-chloromethylfurfural are used, and of these solvents, one or more of amides, ethers and esters, and mixtures thereof are particularly preferred in terms of yield and operation. The amides include for example N,N-dimethylformamide, N,N-diethylformamide, N,N-dimethylacetamide, N-methylpyrrolidone and hexamethylphosphoryl triamide. The ethers include for example diethyl ether, dimethoxyethane, tetrahydrofuran and dioxane. The esters include for example methyl formate, ethyl formate, methyl acetate, ethyl acetate and propyl acetate. These solvents may be used in various combinations such as for example tetrahydrofuran/N,N-dimethylformamide, dioxane/N,N-dimethylformamide, acetone/N,N-dimethylformamide, and toluene/N,N-dimethylformamide mixtures. The amount of the organic solvent used is not particularly limited, but generally, it is preferably within a range of 0.5 to 10 parts by weight based on 5-chloromethylfurfural.

In the more advantageous process of the present invention, 5-chloromethylfurfural is reduced into 5-methylfurfural with hydrogen in an inert organic solvent in the presence of a basic additive and a palladium catalyst. As the inert organic solvent, there are given for example aromatic hydrocarbons and their halides (e.g. benzene, toluene, xylene, chlorobenzene), and halogenated aliphatic hydrocarbons (e.g. methylene chloride, chloroform, carbon tetrachloride). Of these, aromatic hydrocarbons such as benzene, toluene and xylene are preferred. These solvents may be used in combination with alcohols (e.g. methanol, ethanol, isopropanol) or acetic acid. The amount of the organic solvent used is not particularly limited, but generally, it is preferably within a range of 1 to 10 parts by weight based on 5-chloromethylfurfural.

In the still more advantageous process of the present invention, 5-chloromethylfurfural is produced from glucides in place of using it as a starting material, and then converted into 5-methylfurfural. This 5-chloromethylfurfural is a compound which can easily be produced from glucides (e.g. monosaccharide, disaccharide, isomerized saccharide) in a high yield and with high selectivity as disclosed in the foregoing U.S. Pat. No. 4,154,744.

This process is carried out by mixing glucides with hydrochloric acid in the presence of water, an inert organic solvent and a catalytic amount of a surface active agent. Hydrochloric acid may be added in full in advance, or continuously or intermittently with the progress of the reaction. In this case, hydrogen chloride may be introduced into a solution of said glycides in a proper amount of water.

After definite hours' reaction, the aqueous layer is separated from the organic layer, a basic additive and a palladium catalyst are added to the organic layer, and reduction is carried out using hydrogen. Thus, the objective 5-methylfurfural is obtained in a high yield and high purity from the reaction solution.

The saccharides used as a starting material include for example hexoses (e.g. fructose, sorbose, tagatose) and aldohexoses (e.g. glucose, galactose, mannose). Further, deoxysugar, as represented by L-rhamnose and fucose, and its glycosides may be used. As the disaccharides, saccharose, maltose, lactose and the like are used. Further, the so-called isomerized saccharide may also be used, which are obtained by isomerization of glucose with enzyme. Of these, isomerized saccharide, their fructose concentrate, saccharose and fructose are preferred. These materials are cheaply available and the reaction also proceeds easily, so that this process is industrially advantageous.

Hydrochloric acid used in the above decomposition may be a commercial one, and aqueous hydrochloric acid or hydrogen chloride are generally used. The amount of the acid used is generally within a range of 1 to 5 moles based on 1 mole of said glucides, but amounts more than 5 moles have no special advantage.

The organic solvent used in the decomposition of glucides with hydrochloric acid includes inert ones such as for example aromatic hydrocarbons and their halides (e.g. benzene, toluene, xylene, chlorobenzene) and halogenated aliphatic hydrocarbons (e.g. methylene chloride, chloroform, carbon tetrachloride). Of these, aromatic hydrocarbons such as benzene, toluene and xylene are preferred. These solvents may be used in combination with alcohols (e.g. methanol, ethanol, isopropanol) or acetic acid. The amount of the solvent used is not particularly limited, but generally, it is preferably within a range of 1 to 10 parts by weight based on 1 part by weight of the glucides.

The surface active agent as a phase transfer catalyst used in the decomposition of glucides with hydrochloric acid includes for example anionic, cationic, amphoteric and nonionic ones. Of these agents, cationic, amphoteric and anionic ones are particularly preferred.

The cationic surface active agents include for example those of a quaternary ammonium salt type (e.g. lauryltrimethylammonium chloride, cetyltrimethylammonium chloride, cetyldimethylbenzylammonium chloride, tetrabutylammonium bromide, tetrabutylammonium hydrogen sulfate), those of a quaternary phosphonium salt type (e.g. lauryltrimethylphosphonium chloride), those of a pyridinium salt type (e.g. cetylpyridinium chloride) and those of an amine salt type.

The amphoteric surface active agents include for example those of an amino acid type (e.g. sodium laurylaminopropionate) and those of a betaine type (e.g. lauryldimethyl betaine, stearyldimethyl betaine, laurylhydroxyethyl betaine).

The anionic surface active agents include for example alkali metal salts of a higher fatty acid (e.g. sodium laurate, sodium palmitate, sodium stearate), salts of a higher alkyl sulfonic acid (e.g. sodium alkylbenzenesulfonates such as sodium laurylbenzenesulfonate and sodium dodecylbenzenesulfonate), and salts of a higher alcohol sulfuric acid ester (e.g. sodium lauryl sulfate, sodium cetyl sulfate, sodium oleyl sulfate, Teepol type salt of a secondary alcohol).

The nonionic surface active agents include for example those of a polyethylene glycol type (e.g. higher alcohol/ethylene oxide adducts, phenol/ethylene oxide adducts, fatty acid/ethylene oxide adducts) and those of a polyhydric alcohol type (e.g. higher fatty acid sorbitan ester, sugar ester).

These four kinds of surface active agent may be used alone or in combination. When they are used in combination, such combinations as anionic/amphoteric, cationic/amphoteric, anionic/cationic and the like are used. Of these combinations, preferred ones are anionic/cationic and anionic/amphoteric, each of which contains both components in approximately the same amounts. In these cases, the system forms a micellelike state so that the resinification is little and the treatment after reaction is easy. A preferred specific combination is, for example, a mixture of 1 part of a higher alkylsulfonate and 1 part of a quaternary ammonium salt.

The amount of surface active agent used is 1/1000 to 1/10 mole, preferably 1/200 to 1/50 mole, based on 1 mole of said glucides.

The temperature at which decomposition with hydrochloric acid is carried out, is not particularly limited. Heating is preferred to promote the reaction, but the temperature range of 100° C. or less, preferably from about −10° C. to about 80° C. is suitable to inhibit side reactions. Under these conditions, the reaction generally comes to an end in 1 to 25 hours, and at this point, the amount of 5-chloromethylfurfural produced as the intermediate of the reaction of this invention can be analyzed by gas chromatography or other usual methods. In this case, when such a procedure is employed that the glucides and hydrochloric acid are previously mixed and, after adding the surface active agent thereto, added to the heated organic solvent, the reaction proceeds smoothly, making the operation easy.

After definite hours' reaction, the aqueous layer is removed, and reduction is carried out by adding a palladium catalyst and a basic additive to the organic layer containing 5-chloromethylfurfural and then adding hydrogen to the system. Thus, the objective 5-methylfurfural is obtained. The progress of the reaction can be followed up by the amount of hydrogen absorbed, or with the aid of gas chromatography or other usual methods.

As the palladium catalyst used for the reduction of 5-chloromethylfurfural, any of a non-supported type and a supported one may be used independent of the starting material being 5-chloromethylfurfural or glucides. The catalyst may be used in the form of powders or molded products of suitable shape and size. As the non-supported catalyst, for example palladium black, palladium oxide, palladium chloride and the like are used. As the supported catalyst, there are given for example palladium/carbon, palladium/silica, palladium/alumina, palladium/barium sulfate and palladium/calcium carbonate in various ratios of palladium to support. The amount of palladium is not particularly limited, but in the case of batchwise reaction, it is 0.001 to 1 mole, preferably 0.005 to 0.10 mole based on 1 mole of 5-chloromethylfurfural or glucides.

As a preferred basic additive, there is given at least one of organic tertiary amines (e.g. triethylamine, pyridine), alkali metal or alkaline earth metal salts of an inorganic weak acid (e.g. sodium carbonate, potassium carbonate, calcium carbonate), alkali metal or alkaline earth metal salts of an organic acid (e.g. sodium acetate, potassium acetate), alkaline earth metal oxides (e.g. magnesium oxide, calcium oxide), alkali metal hydroxides (e.g. sodium hydroxide, potassium hydroxide) and amides (e.g. N,N-dimethylformamide, N,N-diethylformamide, N,N-dimethylacetamide, N-methylpyrrolidone, hexamethylphosphoryl triamide). Of these compounds, organic tertiary amines, alkali metal salts of an inorganic weak acid or an organic acid and amides are particularly preferably used. The amount of basic additive used is 0.1 to 5 moles, preferably 0.3 to 1.5 moles based on 1 mole of 5-chloromethylfurfural or glucides.

As hydrogen used in the reduction, commercially available one will do. The amount of hydrogen is not particularly limited if it is more than stoichiometric amounts for the simple purpose of completing the reaction. Also, there is no special limitation to the pressure of the reaction, and the reaction proceeds easily even at atmospheric pressure. Pressure may be applied to promote the reaction.

The reduction temperature is not particularly limited, but heating is desirable to promote the reaction. Generally, however, it is within a range of 100° C. or less, preferably −10° C. to 80° C., in order to inhibit side reactions.

The present invention will be illustrated in more detail with reference to the following examples, which are not however to be interpreted as limiting the invention thereto.

EXAMPLE 1

To a four-necked flask equipped with a hydrogen-introducing tube, a cooler, a thermometer and a stirrer was added 6 g (41.5 mmole) of 5-chloromethylfurfural and dissolved in 20 ml of N,N-dimethylformamide. Thereafter, 0.148 g (0.83 mmole) of palladium chloride was added. After replacing atmosphere in the flask with hydrogen, the contents were heated to 40° C. in a water bath, followed by continuing reaction at 40° C. for 3 hours with stirring. During that period, hydrogen was continuously introduced under approximately atmospheric pressure through the tube from a burette filled with water-sealed hydrogen (the quantity of hydrogen required for reaction, 998 ml).

After completion of the reaction, the catalyst was removed, and the reaction solution was quantitatively analyzed by gas chromatography (G.C.-I.S. method using diphenyl ether as an internal standard). As a result, it was found that the yield of 5-methylfurfural was 98% and the conversion of 5-chloromethylfurfural was 99.6%.

EXAMPLE 2

2.06 g (14.26 mmole) of 5-chloromethylfurfural was added to the same flask as used in Example 1 and dissolved in 22.5 ml of tetrahydrofuran. Thereafter, 0.1086 g (0.612 mmole) of palladium chloride was added. After replacing atmosphere in the flask with hydrogen, the contents were heated to 40° C. in a water bath, followed by continuing reaction at 40° C. for 5 hours with stirring. During that period, hydrogen was supplied using the same apparatus as in Example 1 (the quantity of hydrogen consumed, 383 ml). After completion of the reaction, the catalyst was removed, and quantitative determination was carried out by gas chromatography.

Yield of 5-methylfurfural: 95.2%
Conversion of 5-chloromethylfurfural: 100%

EXAMPLE 3

Experiment was carried out under the same condition as in Example 1 using 2 g of 5-chloromethylfurfural, 20 ml of ethyl acetate and 1.179 g of 5% palladium/barium sulfate.

Yield of 5-methylfurfural: 85.7%
Conversion of 5-chloromethylfurfural: 100%

EXAMPLE 4

Experiment was carried out under the same condition as in Example 1 using 2 g of 5-chloromethylfurfural, 20 ml of 1,4-dioxane and 1.179 g of 5% palladium/carbon.

Yield of 5-methylfurfural: 83.5%
Conversion of 5-chloromethylfurfural: 99.1%

EXAMPLE 5

Experiment was carried out under the same condition as in Example 1 except that 2 g of 5-chloromethylfurfural, 0.1104 g of palladium chloride and a mixed solvent of 18 ml of acetone and 2 ml of N,N-dimethylformamide were used, and that the reaction time was 5 hours.

Yield of 5-methylfurfural: 90.2%
Conversion of 5-chloromethylfurfural: 99.0%

EXAMPLE 6

Experiment was carried out under the same condition as in Example 1 except that 2 g of 5-chloromethylfurfural, 0.06 g of palladium black and a mixed solvent of 18 ml of toluene and 2 ml of N,N-dimethylformamide were used, and that the reaction time was 8 hours.

Yield of 5-methylfurfural: 86.1%
Conversion of 5-chloromethylfurfural: 97.3%

EXAMPLE 7

Experiment was carried out under the same condition as in Example 1 using 2 g of 5-chloromethylfurfural, 0.06 g of palladium black and 20 ml of N,N-dimethylacetamide.

Yield of 5-methylfurfural: 97.3%
Conversion of 5-chloromethylfurfural: 100%

EXAMPLE 8

One gram (6.92 mmole) of 5-chloromethylfurfural was added to a four-necked flask equipped with a hydrogen-introducing tube, a cooler, a thermometer and a stirrer, and dissolved in 10 ml of toluene.

Thereafter, 0.37 g (5 mole % based on 5-chloromethylfurfural) of 10% Pd/carbon and 0.567 g (100 mole % based on 5-chloromethylfurfural) of sodium acetate were added. After replacing atmosphere in the flask with hydrogen, the contents were heated to 40° C. in a water bath, followed by continuing reaction at 40° C. for 7 hours with stirring. During that period, hydrogen was continuously introduced under approximately atmospheric pressure through the tube from a burette filled with water-sealed hydrogen (quantity of hydrogen required for reaction, 212 ml).

After completion of the reaction, the catalyst was removed, and the reaction solution was quantitatively analyzed by gas chromatography (G.C.-I.S. method using 1,4-dichlorobutane as an internal standard). The results are shown in Table 1.

TABLE 1

| Product | Yield (%) |
| --- | --- |
| DMFN (2,5-dimethylfuran) | 1.21 |
| ACA (acetonylacetone) | 0.00 |
| MFAL (5-methylfurfural) | 94.75 |
| Unreacted CFAL (5-chloromethylfurfural) | 2.02 |

EXAMPLES 9 to 19

Reaction was carried out in the same manner as in Example 8. The results are shown in Table 2. In the table, DMFN, ACA, MFAL and CFAL have the same meanings as in Table 1.

TABLE 2

| Example No. | Dosage of 5-chloro-methyl-furfural (g) | Solvent Kind | Solvent Dosage (ml) | Catalyst Kind | Catalyst Dosage (mole %) | Additive Kind | Additive Dosage (mole %) | Temperature (°C.) | Time (hr) | Product (yield, %) DMFN | ACA | MFAL | CFAL |
| --- | --- | --- | --- | --- | --- | --- | --- | --- | --- | --- | --- | --- | --- |
| 9 | 1 | Toluene | 10 | 10% Pd/C | 5 | Pyridine | 100 | 40 | 3.5 | 2.1 | 0 | 93.8 | 0 |
| 10 | 1 | " | 10 | " | 5 | K$_2$CO$_3$ | 100 | 17 | 7.0 | 5.2 | 0 | 90.9 | 2.7 |
| 11 | 1 | " | 10 | " | 5 | " | 100 | 40 | 1.5 | 24.6 | 0 | 72.1 | 0 |
| 12 | 1 | Toluene Methanol | 10 5 | " | 5 | KOH | 100 | 35 | 4.5 | 2.5 | 1.1 | 90.9 | 4.1 |
| 13 | 1 | Toluene | 10 | " | 4.6 | Triethylamine | 150 | 35 | 2.5 | 0.1 | 0 | 98.8 | 0 |
| 14 | 1 | " | 10 | 5% Pd/C | 5.5 | " | 90 | 40 | 3.5 | 0 | 0 | 95.6 | 0.9 |
| 15 | 1 | " | 10 | 10% Pd/C | 5 | MgO | 100 | 40 | 5.5 | 2.7 | 0.5 | 91.6 | 1.1 |
| 16 | 1 | " | 10 | PdCl$_2$ | 5 | Sodium acetate | 100 | 40 | 3.5 | 1.6 | 0 | 92.4 | 0.9 |
| 17 | 1 | " | 10 | 5% Pd/BaSO$_4$ | 5 | Triethylamine | 50 | 45 | 6.5 | 1.7 | 0 | 88.1 | 4.9 |
| 18 | 1 | Xylene | 10 | 10% Pd/C | 5 | Na$_2$CO$_3$ | 90 | 20 | 7.0 | 4.3 | 0 | 91.7 | 1.6 |
| 19 | 1 | Chloroform | 10 | " | 5 | Triethylamine | 100 | 35 | 3.0 | 0.7 | 0 | 93.6 | 0 |

EXAMPLE 20

To a three-necked flask equipped with a cooler and a stirrer were added 5 g (0.028 mole) of a commercially available D-(−)fructose and two kinds of surface active agent, i.e., 89.6 mg (0.00028 mole) of cetyltrimethylammonium chloride and 97.6 mg (0.00028 mole) of sodium laurylbenzenesulfonate. Then, 5 ml of water and 30 ml of toluene were added thereto and the mixture was stirred. Thereafter, an excess amount of hydrogen chloride (about 15 g) was passed through the mixture at room temperature for about 40 minutes with thorough stirring. After stirring was continued at room temperature for further 2.5 hours, the upper toluene layer was separated from the lower aqueous layer. Thirty milliliters of toluene and the above two surface active agents of the same amounts as above were then freshly added to the aqueous layer. After the mixture was stirred for 2.5 hours at room temperature, the upper toluene layer was again separated. This toluene extraction operation was repeated three times in total. All the toluene layers (hydrochloric acid-acidic liquor) were combined and added to a four-necked flask equipped with a hydrogen-introducing tube, a cooler, a thermometer and a stirrer. Then, 1.37 g (about 4.6 mole % based on fructose) of 10% palladium/carbon and 2.81 g (100 mole % based on fructose) of triethylamine were added. After replacing atmosphere in the flask with hydrogen, the contents were heated to 35° C. in a water bath, followed by continuing reaction at 35° C. for about 30 minutes with stirring. During that period, hydrogen was continuously introduced under approximately atmospheric pressure through the tube from a burette filled with water-sealed hydrogen (quantity of hydrogen absorbed, 815 ml).

After completion of the reaction, the catalyst was removed, and the reaction solution was quantitatively analyzed by gas chromatography. As a result, it was found that the yield of 5-methylfurfural was 75% based on the saccharide used as a starting material with no formation of by-products.

EXAMPLE 21

Ten grams (0.056 mole) of a commercially available D-(−)-fructose and 23.3 g (4 equivalents based on fructose) of conc. hydrochloric acid (commercially available special grade) were mixed and slowly stirred at about 20° C. for 2 hours. Thereafter, 0.1 g of Cotamine 24P (27.5% aqueous lauryltrimethylammonium chloride solution), a cationic surface active agent produced by Kaō-Atlas Co., was added, followed by stirring for further 15 minutes. This reaction solution was taken as "pre-reaction solution".

Separately from this, 100 ml of toluene was added to a four-necked flask equipped with a cooler, a thermometer and a stirrer, and kept at 80° C. in an oil bath. Immediately after completion of the above reaction, the pre-reaction solution was added dropwise to this flask over about 20 to 30 minutes, followed by stirring for about 10 minutes at the same temperature. After the temperature of the solution was allowed to linearly drop to room temperature with stirring (in about 1 to 2 hours), a little water was added, followed by stirring and standing.

After the aqueous layer (lower layer) was separated, 2.74 g (about 4.6 mole % based on fructose) of 10% palladium/carbon and 5.62 g (100 mole % based on fructose) of triethylamine were added to the toluene layer. After equipping this four-necked flask with a hydrogen-introducing tube and replacing atmosphere in the flask with hydrogen, the contents were heated to 35° C. in a water bath, followed by continuing reaction at 35° C. for about 1 hour with stirring. Hydrogen was introduced in the same manner as in Example 20. The quantity of hydrogen absorbed was about 1448 ml.

After completion of the reaction, quantitative analysis was carried out by gas chromatography. As a result, it was found that the yield of 5-methylfurfural was 66.7% based on the saccharide used as a starting material with no formation of by-products.

EXAMPLES 22 to 31

Reaction was carried out in the same manner as in Example 20 or 21. The results are shown in Table 3. The yields of the products, DMFN (2,5-dimethylfuran), MFAL (5-methylfurfural) and CFAL (5-chloromethylfurfural) are based on the saccharide as a material.

TABLE 3

| Example No. | Saccharide Kind | Saccharide Dosage (g) | Hydrogen chloride gas (g) | Conc. hydrochloric acid (35%) (g) | Surface active agent Kind | Surface active agent Dosage (g) | Organic solvent Kind | Organic solvent Dosage (ml) | Method of Example 20 (extraction-addition) | Method of Example 21 (pre-reaction/dropwise addition) |
|---|---|---|---|---|---|---|---|---|---|---|
| 22 | Crystalline fructose (commercially available D-(−)-fructose) | 10.0 | | 23.3 | Cotamine 24P | 0.1 | Toluene | 100 | | Pre-reaction, 20° C. × 2 hrs; dropwise addition, 60° C. × 1 hr; temperature-maintenance, 60° C. × 1 hr |
| 23 | Crystalline fructose | 10.0 | | 23.3 | Cotamine 24P | 0.1 | Toluene | 100 | | Pre-reaction, 20° C. × 2 hrs; dropwise addition, 70° C. × 0.5 hr; temperature-maintenance, 70° C. × 0.5 hr |
| 24 | Crystalline fructose | 10.0 | | 23.3 | Cetyltrimethyl-ammonium chloride | 0.12 | Benzene | 60 | | Pre-reaction, 20° C. × 2 hrs; Dropwise addition, 60° C. × 1 hr; temperature-maintenance, 60° C. × 1 hr |
| 25 | High fructose syrup (solid content 75.8%; fructose 90%) | 14.7 | | 23.3 | Cotamine 24P | 0.1 | Toluene | 100 | | Pre-reaction, 0.5° C. × 20 hrs; dropwise addition, 80° C. × 0.5 hr; temperature-maintenance, 80° C. × 0.2 hr |
| 26 | High fructose syrup (solid content 75.8%; fructose 90%) | 14.7 | | 23.3 | Cetyltrimethyl-ammonium chloride<br>Sodium lauryl-benzene-sulfonate | 0.08<br>0.09 | Toluene | 100 | | Pre-reaction, 0–5° C. × 20 hrs; dropwise addition, 80° C. × 0.3 hr; temperature-maintenance, 80° C. × 0.2 hr |
| 27 | D-(+)-saccharose | 5.0 | 15.0 | | Same as above<br>Same as above | 0.05<br>0.05 | Toluene<br>Water | 30<br>5 | HCl(g) introduced at room temperature in 3 hours; toluene extraction, 3 times | |
| 28 | D-(+)-galactose | 5.0 | 12.7 | 6 ml | Same as above | Same as above | Same as above | Same as above | 35% HCl(6 ml) added dropwise at room temperature in 1 hour; HCl (g) introduced at 50° C. in 3 hours; toluene extraction, 2 times | |
| 29 | L-(−)-sorbose | 2.5 | 12.7 | 6 ml | Same as above | Same as above | Same as above<br>CCl₄ | Same as above<br>30 | Same as above | |
| 30 | D-(−)-fructose | 10.0 | 14.7 | 23.3 | Sodium laurate<br>Tetrabutyl-ammonium bromide | 0.06<br>0.09 | CCl₄<br>Water | 30<br>5 | HCl(g) introduced at room temperature in 0.5 hour; CCl₄ extraction, 2.5 hr × 3 times | |
| 31 | D-(−)-fructose | 10.0 | | 23.3 | Cotamine 24P | 0.1 | Toluene | 80 | | Pre-reaction, 20° C. × 2 hrs; dropwise addition, 80° C. × 0.3 hr; temperature-maintenance, 80° C. × 0.2 hr |

TABLE 3-continued

| Example No. | Palladium catalyst Name Dosage (g) | Additive Name Dosage (g) | Condition Reaction temperature (°C.) | Reaction time (hr) | Yield of products (%) DMFN | MFAL | CFAL |
|---|---|---|---|---|---|---|---|
| 22 | 10% Pd/C 2.74 | N,N-dimethylformamide 4.1 | 35 | 1.5 | 6.97 | 57.5 | 0 |
| 23 | 10% Pd/C 2.74 | CH$_3$COONa 4.55 | 40 | 3.5 | 1.29 | 61.7 | 1.10 |
| 24 | 10% Pd/C 2.74 | Triethylamine 5.62 | 40 | 3.0 | 0.0 | 56.3 | 0 |
| 25 | 5% Pd/C 5.72 | Pyridine 4.38 | 40 | 1.5 | 1.03 | 64.1 | 0 |
| 26 | PdCl$_2$ 0.30 | K$_2$CO$_3$ 7.67 | 17 | 7.0 | 2.47 | 63.7 | 0.59 |
| 27 | 10% Pd/C 2.70 | Triethylamine 2.81 | 40 | 2.5 | 0.09 | 59.4 | 0.98 |
| 28 | 10% Pd/C 2.70 | Na$_2$CO$_3$ 5.88 | 40 | 3.5 | 1.28 | 49.3 | 1.31 |
| 29 | 10% Pd/C 2.70 | Na$_2$CO$_3$ 5.88 | 40 | 4.5 | 0.87 | 52.9 | 0.23 |
| 30 | 5% Pd/BaSO$_4$ 5.89 | Triethylamine 2.81 | 50 | 4 | 5.47 | 49.8 | 2.03 |
| 31 | 10% Pd/C 3.0 | KOH/CH$_3$OH 3.1/30 | 35 | 4 | 3.95 | 58.78 | 4.17 |

What is claimed is:

1. A process for producing 5-methylfurfural which comprises that 5-chloromethylfurfural is reduced with hydrogen in an organic solvent in the presence of a palladium catalyst.

2. A process according to claim 1, wherein one or more of amides, ethers and esters are used as said organic solvent.

3. A process according to claim 1 or 2, wherein a mixed solvent containing at least one of amides, ethers and esters is used as said organic solvent.

4. A process for producing 5-methylfurfural which comprises that hydrogen is allowed to act on 5-chloromethylfurfural using a palladium catalyst in the presence of an inert organic solvent containing a basic additive.

5. A process for producing 5-methylfurfural which comprises that monosaccharide, disaccharide or isomerized saccharide is decomposed with hydrochloric acid in a water/organic solvent/surface active agent (catalyst) system, and after adding a basic additive to the organic layer which has been separated from the aqueous layer, reduced with hydrogen in the organic layer in the presence of a palladium catalyst.

6. A process according to claim 4 or 5, wherein the basic additive is at least one of tertiary amines, amides, alkali metal or alkaline earth metal salts of an inorganic weak acid or organic acid, alkaline earth metal oxides and alkali metal hydroxides.

* * * * *